United States Patent [19]

Magnussen, Jr.

[11] Patent Number: 5,064,287

[45] Date of Patent: Nov. 12, 1991

[54] SAMPLE FLOW CELL WITH CIRCUMFERENTIALLY UNIFORM RADIAL FLOW PATTERN AT ITS ENTRANCE AND/OR EXIT PORTS

[75] Inventor: Haakon T. Magnussen, Jr., Orinda, Calif.

[73] Assignee: Rainin Instrument Co., Inc., Emeryville, Calif.

[21] Appl. No.: 510,053

[22] Filed: Apr. 16, 1990

[51] Int. Cl.⁵ ............................................. G01N 21/05
[52] U.S. Cl. .................................................... 356/246
[58] Field of Search ................. 356/246; 350/584, 319

[56] References Cited

U.S. PATENT DOCUMENTS

| | | | |
|---|---|---|---|
| 3,647,304 | 3/1977 | Emmel et al. | 356/246 |
| 4,240,691 | 12/1980 | Holmquist et al. | 350/584 |
| 4,315,692 | 2/1982 | Hemecke et al. | 350/584 |
| 4,374,620 | 2/1983 | Berick et al. | 356/246 |

Primary Examiner—Richard A. Rosenberger
Attorney, Agent, or Firm—Robert R. Meads

[57] ABSTRACT

A fluid sample flow cell characterized by a circumferentially uniform radial fluid flow into an entry port to and/or from an exit port from a fluid passageway through the body of the cell.

8 Claims, 5 Drawing Sheets

SAMPLE FLOW CELL WITH CIRCUMFERENTIALLY UNIFORM RADIAL FLOW PATTERN AT ITS ENTRANCE AND/OR EXIT PORTS

BACKGROUND

The problems associated With non-uniform sample fluid flow at the entrance ports to photometric flow cells are Well known and as listed in U.S. Pat. No. 4,374,620 include (1) instability in the optical base line between measurements of successive fluid fractions, (2) mixing between successive fractions, (3) formation of air bubbles in the flow cell passageway, and (4) formation of dead pockets at corners in the flow passageway Which require relatively large volumes of fluid to totally sweep or flush each sample from the passageway.

In the '620 patent, the foregoing problems are addressed by the inclusion of a microporous annulus in the fluid inlet channel surrounding the entrance and/or exit port to and/or from the fluid passageway for receiving and passing fluid samples through the flow cell. Unfortunately, in practice, the economic manufacture of the microporous annulus has not been achieved nor has reliable fluid tight sealing of the marginal edges of the annulus in the inlet channel. For these reasons, the approach proposed by the '620 patent has not been commercially implemented.

Another approach to the foregoing problems is described and illustrated in an earlier U.S. Pat. No.3,647,304. The '304 patent proposes a cylindrical insert having an inlet and an outlet and each defining a plurality of openings channelling to a generally cylindrical fluid chamber formed within the insert. The openings in the inlet are elongated and equidistantly disposed about the periphery of the inlet to provide a laminar fluid flow therethrough into the fluid chamber. While in theory it appears that the insert will reduce non-uniformities in fluid flow within the flow cell, the inlet flow of fluid through the plurality of equidistantly disposed radially extending openings is uneven. Moreover, the insert requires special and expensive manufacturing and introduces additional assembly expenses to the overall costs of the flow cell.

Accordingly, there is a continuing need for a low cost reliable solution to the problems associated with non-uniform entry and exit flow into and from fluid sample flow cells. The present invention satisfies that need.

SUMMARY OF INVENTION

The present invention satisfies the foregoing need by providing a fluid sample flow cell including an entrance and/or exit port fluid distributor for passing fluid from a fluid inlet in a circumferentially uniform radial pattern into an entry port to the fluid passageway through the flow cell and/or passing fluid from the fluid passageway to a fluid outlet in a circumferentially uniform radial pattern from an exit port from the passageway. The distributor comprises a hollow fluid distribution ring connected to the inlet and/or outlet and including an annular slot around an inner annular side of the ring contiguous with an annular nozzle open at an outer annular edge to the distribution ring and at an inner annular edge to the entry and/or exit port. The distribution ring defines a relatively low fluid flow impedance annulus between the inlet or outlet and the nozzle and the nozzle defines a radially open relatively high fluid flow impedance annulus between the distributor ring and the port. When the fluid distributor is at the entry port fluid from the inlet first flows circumferentially around the entry port in the distribution ring and then in a circumferentially uniform radial pattern inwardly through the nozzle into the entry port. When the fluid distributor is at the exit port, fluid from the exit port flows in a circumferentially uniform radial pattern outwardly through the nozzle into the distributor ring and circumferentially in the ring around the exit port into the fluid outlet.

DETAILED DESCRIPTION OF PREFERRED EMBODIMENTS OF INVENTION

Figure 1:
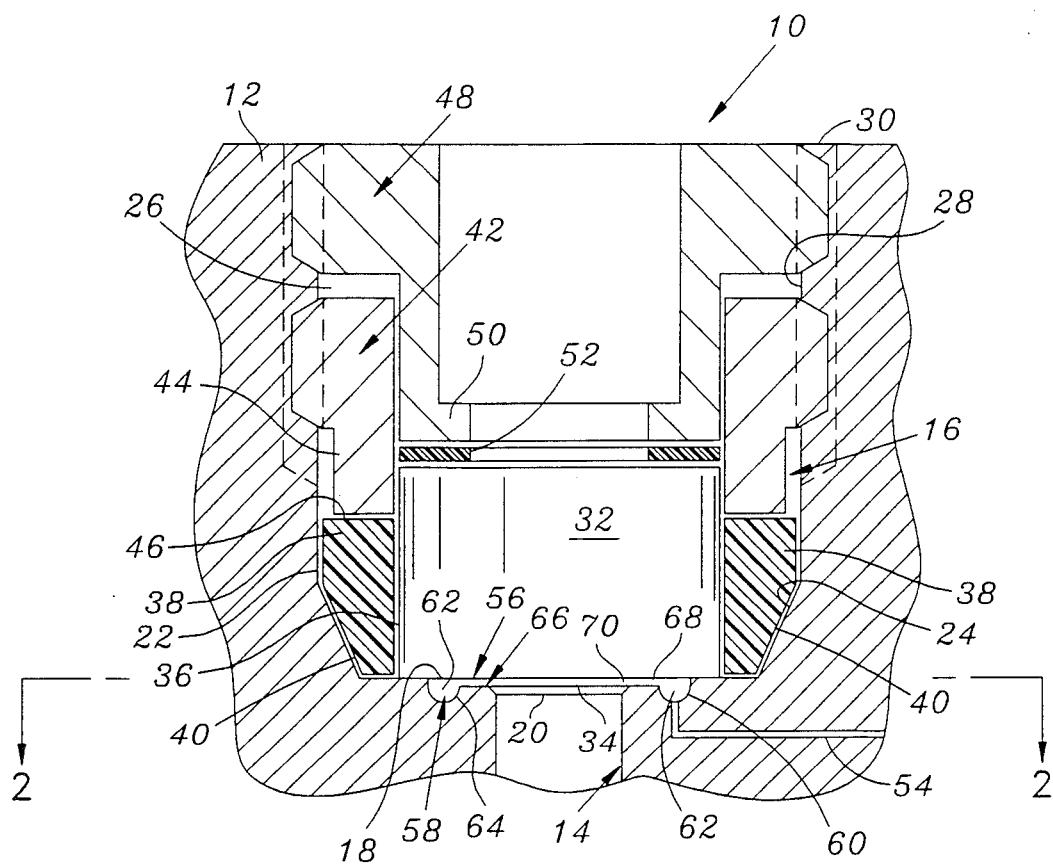
FIG. 1 is a cross section along line 1—1 in FIG. 2 of a portion of a first embodiment of a fluid sample flow cell in accordance with the present invention. The illustrated portion may comprise either the entry port or exit port portion of the flow cell, one or both portions including the fluid distributor of the present invention.

In the drawings, the flow cell in accordance with the present invention is represented by the number 11 and includes a circumferential window edge seal as described in the co-pending patent application, serial number 07/510,038, filed concurrently with and assigned to the same assignee as the present application. As there described, the flow cell 10 comprises a chemically inert metal cell body 12 having a passageway 14 therethrough.

Connecting to the passageway 14 is a window receiving cavity 16. The cavity 16 includes (i) an annular inner end 18 surrounding an entry or exit port 20 to the passageway 14, (ii) an inner end portion 22 including an inner axially extending annular surface 24 diverging radially outwardly and (iii) an outer end portion 26 including a axially extending internally threaded annular surface 28 adjacent an outer end 30 of the cavity.

Seated in the inner end portion 22 of the cavity 16 is a cylindrical window 32. The window may be formed of quartz and includes a flat end face 34 over the inner end 18 of the cavity and a cylindrical circumferential edge 36 adjacent to the inner annular surface 24 of the cavity.

Seated around the circumferential edge 36 of the window 32 and adjacent to the inner annular surface of the cavity is an annular slightly deformable ferrule 38. The ferrule 38 preferably is formed from a chemically inert plastic and includes an axially extending outer surface 40 divering radially outwardly for mating with the outwardly diverging annular surface 24 of the cavity.

In order to create the desired circumferential window edge seal, a metal ferrule clamp 42 comprising a tubular screw is threaded into the outer end portion 26 of the cavity with an annular end 44 of the clamp pressing axially on an outer end 46 of the ferrule 38. As the ferrule clamp is tightened in the cavity 16, the annular end 44 exerts a sufficient force on the ferrule as to wedge it tightly between the circumferential edge 36 of the window 32 and the annular surface 24 of the cavity creating a high pressure fluid tight seal therebetween.

To secure the window 32 within the window receiving cavity 16, a window clamp 48 comprising a tubular metal screw is threaded into the outer end portion 26 of the cavity with an inner annular end 50 pressing axially on an annular window pad 52 to create a restraining force against the window.

Figure 2:
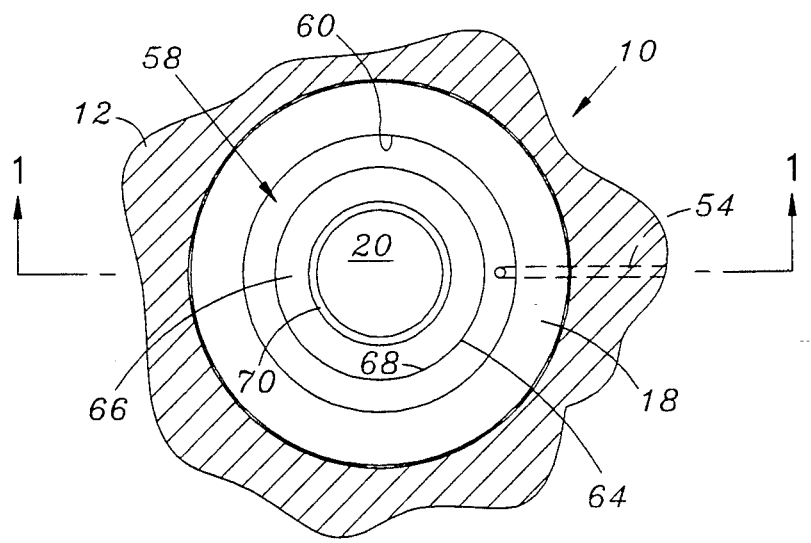
FIG. 2 is a cross section taken along the line 2—2 in FIG. 1.

Depending upon whether the end portion of the flow cell illustrated in FIGS. 1 and 2 is the entry or exit portion, to provide means for introducing or withdrawing fluids samples into or from the entrance port 20, the flow cell 10 includes a fluid inlet or outlet 54. When functioning as an inlet, 54 may be connected to a fluid sample source such as a LC column. As previously indicated, it is important that the flow of fluid samples in the port 20 be uniformly distributed to minimize dead volumes and to minimize sweep out volumes. In accordance with the present invention, a fluid distributor 56 is included in the entry and/or exit portions of the flow cell 10 for passing fluid in a circumferentially uniform radial pattern into or out of the port 20.

Generally speaking, the fluid distributor includes means defining a hollow fluid distribution ring 58 connecting at an outer annular edge 60 to the fluid inlet o outlet 54. The distribution ring 58 includes an annular slot 62 around an inner annular side 64 of the ring contiguous with an annular nozzle 66 completely open at an outer annular edge 68 to the distribution ring and completely open at an inner annular edge 70 to the por 20.

The distribution ring is dimensioned to define a relatively low fluid flow impedance annulus between the inlet or outlet 54 and the nozzle 66 and the nozzle is dimensioned to define a radially open relatively high fluid flow impedance annulus between the distribution ring and the port 20. Thus, fluid from the inlet 54 first flows circumferentially around the entry port in the distribution ring 58 and then in circumferentially uniform radial pattern inward through the nozzle 66 into the entry port 20. Similarly, fluid from the passageway 14 flows in a circumferentially uniform radial pattern outwardly through the nozzle 66 and into the distribution ring 58 at the exit portion of the flow cell and then circumferentially around the exit port to the fluid outlet.

More particularly, as illustrated in FIGS. 1 and 2 for a first embodiment of the present invention in the entry portion of the flow cell 10, the annular nozzle 66 is defined by an annular gap between a flat annular face comprising an annular relief in the inner end 18 of the window receiving cavity 16 immediately surrounding the entrance port 20 and an opposing flat annular face on the window 32. The distribution ring 58 is defined by an outer annular semicircular channel formed in the inner end 18 of the window receiving cavity radially outward of the annular gap in combination with the flat end face of the window 32 covering the annular channel. In this regard, it should be noted that the annular slot 62 is defined by the annular opening at the top of the channel below the end face of the window 32 along the radially innermost annular side of the channel and that the slot thus defined is completely open to and contiguous with the outermost radial edge portion of the annular gap. As illustrated, the inlet 54 is connected to and communicates with the bottom of the annular channel such that fluid passing through the inlet enters the channel and first travels circumferentially therearound and then in a circumferentially uniform radial pattern inwardly through the annular gap to the open end of the entry port 20.

Figure 3:
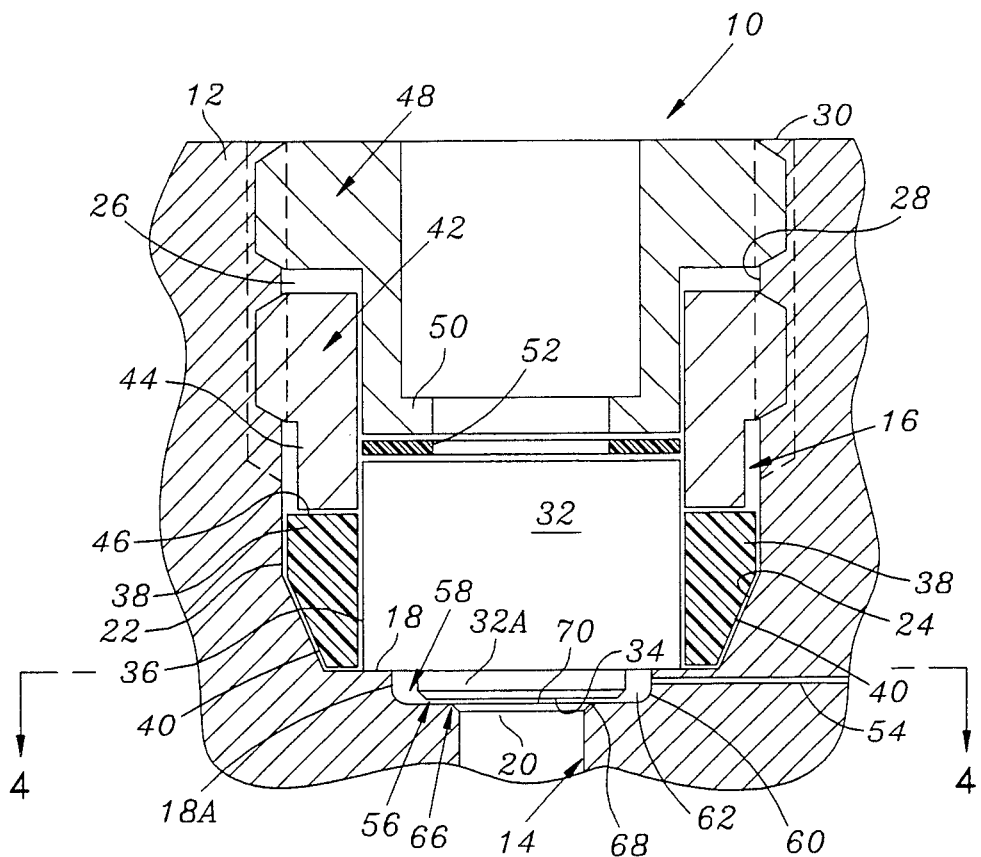
FIG. 3 is a cross section along the line 3—3 in FIG. 4 of a portion of a second embodiment of a fluid sample flow cell in accordance with the present invention. Like FIG. 1 the portion illustrated in FIG. 3 may comprise either the entry port or exit port portion of the flow cell.
Figure 4:
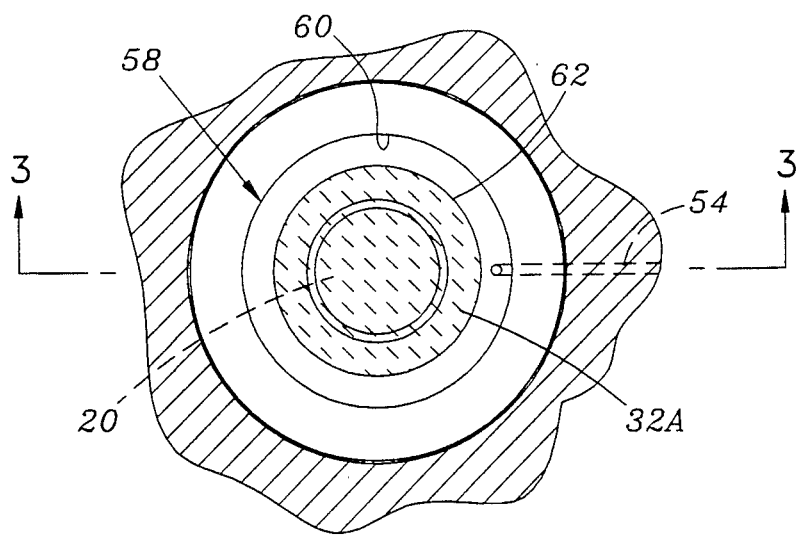
FIG. 4 is a cross section taken along the line 4—4 in FIG. 3.
Figure 5:
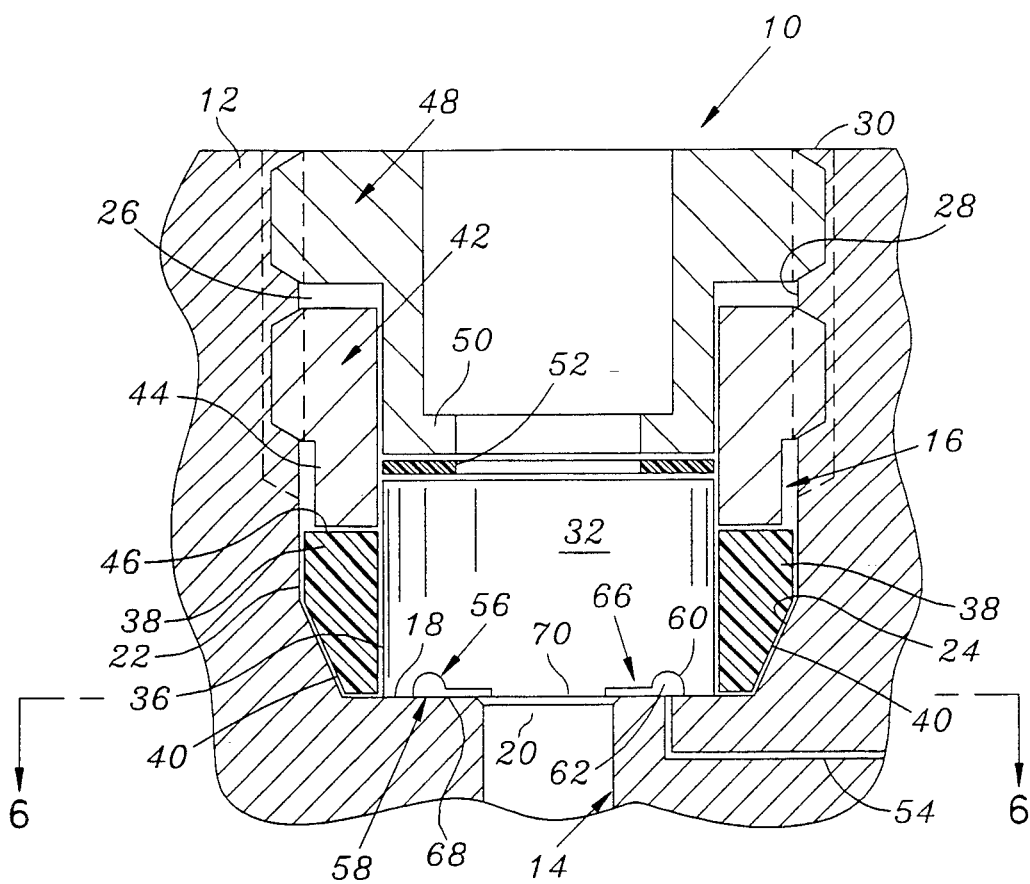
FIG. 5 is a cross section along the line 5—5 in FIG. 6 of a portion of a third embodiment of a fluid sample flow cell in accordance with the present invention. Like FIG. 11, the portion illustrated in FIG. 5 may comprise either the entry or exit portion of the flow cell.
Figure 6:
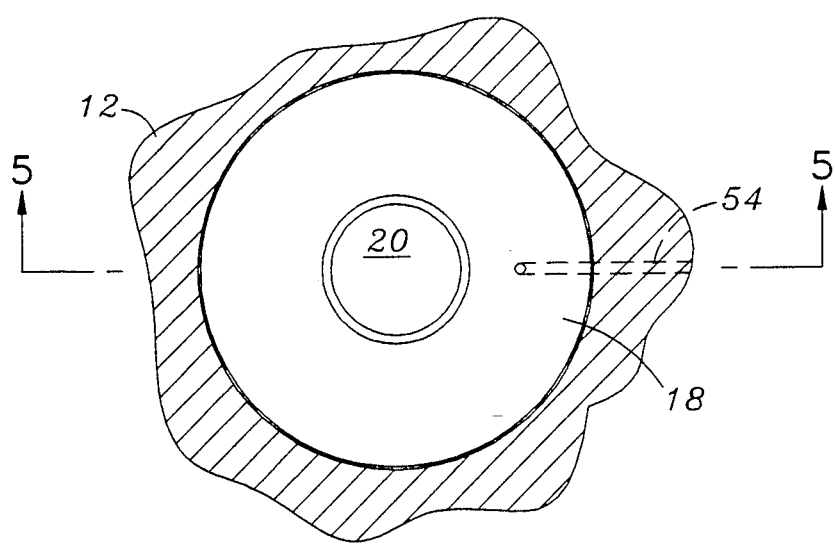
FIG. 6 is a cross section taken along the line 6—6 in FIG. 5.
Figure 7:
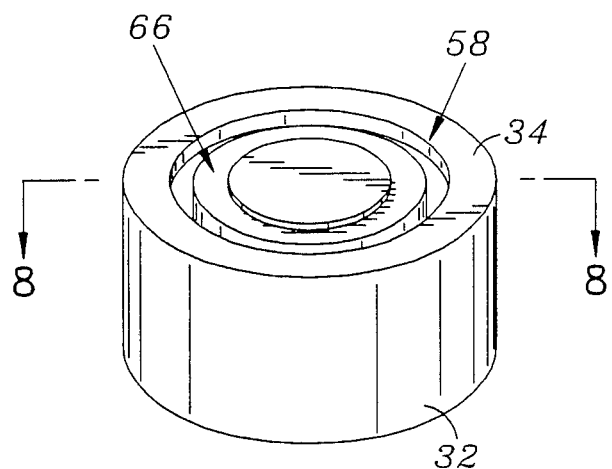
FIG. 7 is a perspective view of a window included in the flow cell of FIGS. 5 and 6 showing an annular fluid distribution ring and a face of a annular gap open to an entry or exit port in the flow cell.
Figure 8:
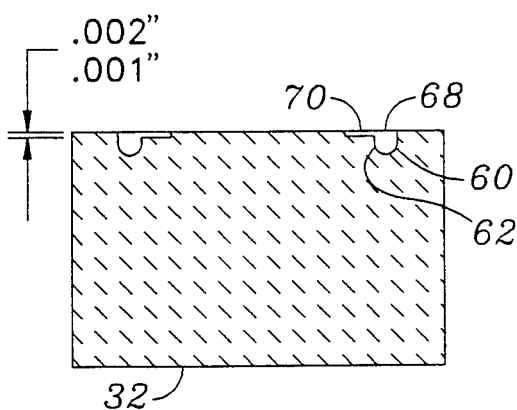
FIG. 8 is a cross section taken along the line 8—8 in FIG. 7.

As illustrated in FIGS. 3 and 4 for a second embodiment of the present invention, the distribution ring 58 is defined by an axially extending annular gap surrounding an axial extension 32A of the window 32 formed by an annular marginal relief in the window. The annular extension 32A extends into the annular relief in the inner end 18 of the window receiving cavity 16 surrounding the port 20. Thus constructed, the outer annular channel is formed between an inner concave surface of an annular shoulder 18A and the outer surface of the cylindrical extension 32A of the window while the annular nozzle 66 is defined by an annular gap formed between the flat annular face of the inner end 18 immediately surrounding the entrance port 20 and an opposing flat annular face on the window extension. In construction, the thickness of the annular gap is defined by the difference between the height of the shoulder 18A and the length of the window extension 32A. The fluid inlet or outlet 54 connects to an outermost annular side of the annular channel. Thus, as described for the embodiment illustrated in FIGS. 1 and 2, when the portion of the flow cell illustrated in FIGS. 3 and 4 comprises the entry portion, fluid passing through the inlet 54 enters the annular channel and travels circumferentially therearound and then in a circumferentially uniform radial pattern through the annular gap and into the open end of the entry port 20. When the illustrated portion comprises the exit portion of the flow cell, fluid from the passageway 14 flows in a circumferentially uniform radial pattern outwardly through the annular gap defining the nozzle 66 and then circumferentially around the distribution ring 58 into the fluid outlet 54.

As illustrated is FIGS. 5, 6, 7 and 8, the distribution ring 58 is defined by an outer annular semicircular channel formed in the flat end face 34 of the window 32 and the annular nozzle 66 is defined by an annular gap formed between the flat annular face in the end 18 of the window receiving cavity surrounding the port 20 and an annular relief in the end face of the window radially within the outer annular channel. The fluid inlet or outlet 54 connects to the outer annular channel at the bottom of the channel along the outermost sidewall thereof such that When the illustrated portion of the flow cell comprises the entry portion, fluid flowing through the inlet first travels circumferentially around the annular channel and then in a circumferentially uniform radial pattern inwardly through the annular gap to the open end of the entry port 20. Similarly, when the illustrated portion of the flow cell comprises the exit portion, fluid from the passageway 14 flows in a circumferentially uniform radial pattern outwardly through the annular gap to the annular channel and circumferentially therearound to the fluid outlet.

Figure 9:
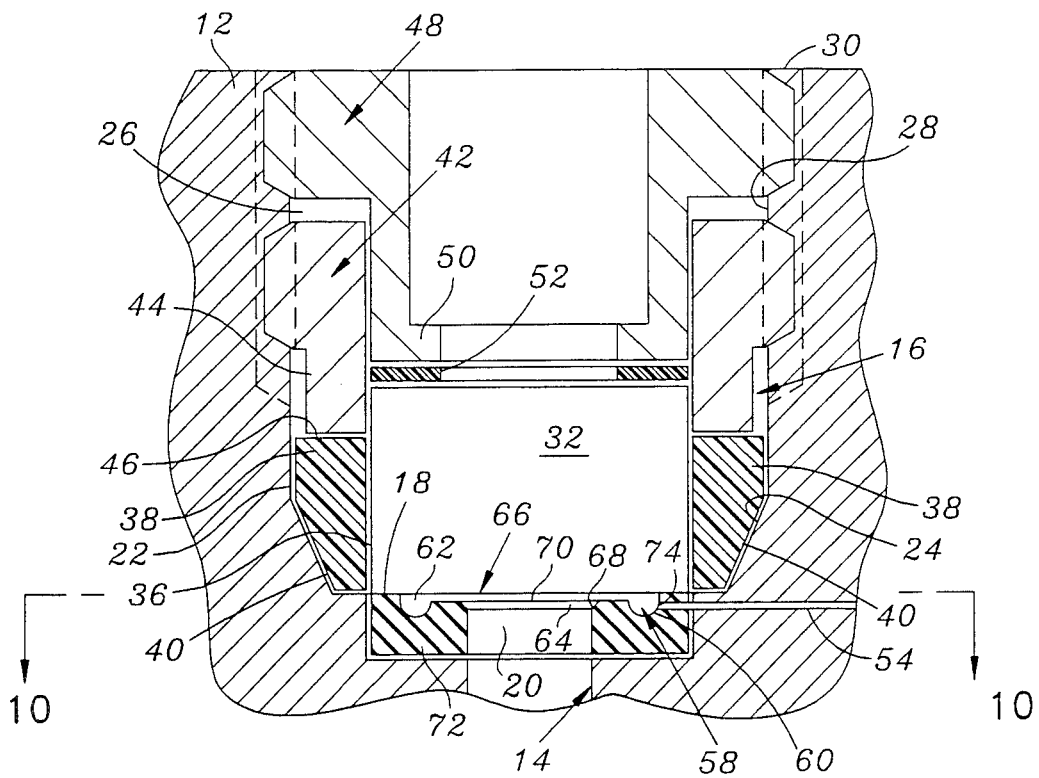
FIG. 9 is a cross section along the line 9—9 in FIG. 10 of a portion of a forth embodiment of a fluid sample flow cell in accordance with the present invention. Like FIG. 1, the portion illustrated in FIG. 9 may comprise either the entry or exit portion of the flow cell.
Figure 10:
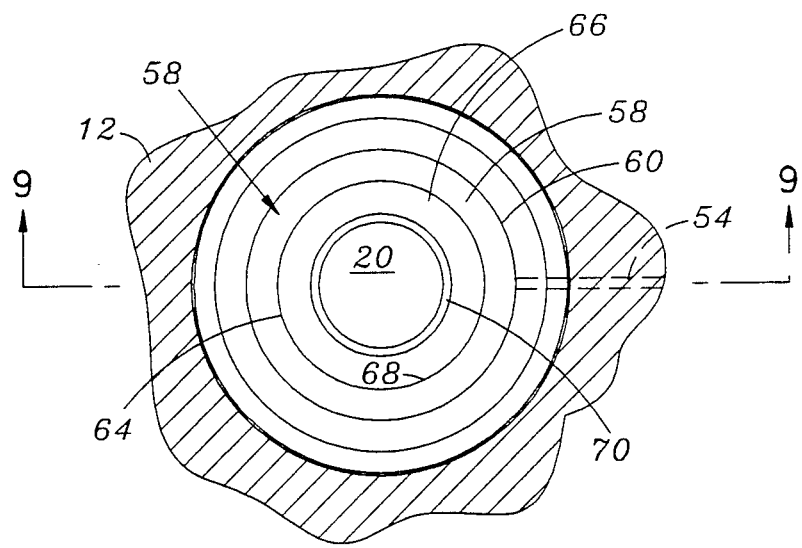
FIG. 10 is a cross section taken along the line 10—10 in FIG. 9.

As illustrated in FIGS. 9 and 10 for a fourth embodiment of the present invention, the distributor ring 58 and nozzle 66 are of a structure similar to that illustrated in FIGS. 1 and 2 except that they are formed in an annular insert adjacent the end face 34 of the window 32. In that reward, the fluid distributor 56 illustrated in FIGS. 9 and 10 includes an annular insert 72 for mounting in the window receiving cavity 16 below the window 32 on the inner end 18 of the cavity. In the insert 72, the distribution ring 58 includes an outer annular semicircular channel in a top face of the insert while the annular nozzle includes an annular relief in the top surface open to and radially within the outer annular channel for combining with the annular face of the window 32 above the insert. When the illustrated portion of the flow cell comprises the entry portion thereof, the fluid inlet 54 communicates With a side port 74 in the insert leading to the outermost side of the annular channel for passing fluid from the inlet into the outer annular channel Where it travels circumferentially around the entry port 20 and then in a circumferentially uniform radial pattern through the annular gap into the entry port. When the illustrated portion comprises the exit portion of the flow cell, fluid from the passageway 14 travels through the exit port and in a circumferentially uniform radial pattern outwardly through the annular gap into the annular channel Where it travels circumferentially around the exit port to the fluid outlet.

In each of the foregoing embodiments, it should be noted that the distribution ring 58 defined by the annular channel forms a relatively low fluid flow impedance annulus between and completely open to an inner side of a relatively high fluid flow impedance annulus formed by the annular gap. In this regard, the axial dimension of the annular gap preferably is between 0.001 and 0.002 inches and the axial dimension of the annular channel is characterized as being at least twice that of the annular gap or greater than 0.002 to 0.004 inches. Further, the annular gap is characterized by axial dimension less that one-half its radial dimension and annular channel is characterized by a axial dimension about equal to its radial dimension.

While particular forms of the present invention have been described in detail hereinabove, such description is by way of example only. Changes and modifications may be made in the illustrated embodiments without departing from the spirit or scope of the present invention as defined by the following claims.

I claim:

1. A fluid sample flow cell comprising:
   a cell body including a fluid passageway therethrough;
   a window having an end face seated over a port to the passageway; and
   a fluid distributor comprising a hollow fluid distribution ring connected to a fluid inlet or outlet and including an opening in an inner annular side of the ring contiguous With an annular nozzle open at an outer annular edge to the distribution ring and at an inner annular edge to the port, the ring defining a relatively low fluid flow impedance annulus between the fluid inlet or outlet and the nozzle and the nozzle defining a relatively high fluid flow impedance annulus between the ring and the port whereby when the distribution ring is connected to a fluid inlet fluid from the inlet first flows circumferentially around the entrance port in the distribution ring and then in a circumferentially uniform radial pattern inwardly through the nozzle into the port and when the distribution ring is connected to a fluid outlet, fluid flows from the passageway through the port and in a circumferentially uniform radial pattern outwardly through the nozzle to the distribution ring and circumferentially around the port to the fluid outlet.

2. A fluid sample flow cell characterized by circumferentially uniform radial fluid flow into an entry port to a fluid passageway through the cell and/or circumferentially uniform radial fluid flow from an exit port from the fluid passageway to a fluid outlet for the cell, comprising:
   a cell body having a fluid passageway therethrough;
   a window seated over entry and exit ports to and from the fluid passageway; and
   fluid distributor means for distributing fluid circumferentially around and in a circumferentially uniform and radial pattern into the entry port and/or from the exit port, the fluid distributor means comprising
   an annular gap between an annular face surrounding at least one of the entry and exit ports and an opposing annular face on the window seated over the one port, the gap defining a relatively high fluid flow impedance annulus surrounding the one port and
   outer annular channel means having a portion of a radially innermost annular side thereof open to and contiguous with an outermost radial edge portion of the annular gap, the channel defining a relatively low fluid flow impedance annulus between and open on an inner annular side to the high fluid flow impedance annulus, a fluid inlet or outlet being connected to the outer channel means whereby fluid flows into or from and circumferentially around the outer channel and in a circumferentially uniform radial pattern through the annular gap into or from the one port.

3. The flow cell of claim 2 wherein the annular gap is completely open to the one port.

4. The flow cell of claim 2 wherein the annular gap is characterized by an axial dimension less than onehalf it radial dimension and the annular channel is characterized by a axial dimension about equal to its radial dimension.

5. The flow cell of claim 2 wherein:
   the window is seated on an annular surface on the cell body;
   the outer annular channel is formed in a top of the annular surface; and
   the annular gap is formed between a bottom face of the window and annular relief in the annular surface around the one port.

6. The flow cell of claim 2 wherein:
   the window is seated on top of an annular shoulder on the cell body;

the outer annular channel is formed between an inner surface of the annular shoulder and an outer surface of a cylindrical extension of the window over the one port; and the annular gap is formed between the annular face surrounding the one port and an opposing annular face on the window extension.

7. The flow cell of claim 2 wherein:

the window is seated on an annular surface on the cell body;

the outer annular channel is formed in a bottom surface of the window; and the annular gap is formed between the annular face surrounding the one port and an annular relief in the bottom surface of window radially within the outer annular channel.

8. The flow cell of claim 2 wherein the distributor means comprises an annular insert for mounting in a bottom of a window receiving cavity in the body of the flow cell between the window and the one port, the insert including an annular channel in a top face thereof defining the outer annular channel and an annular relief in a top surface open to and radially within the outer annular channel for combining with the annular face of the window to define the annular gap.

* * * * *